United States Patent
Klausz et al.

(10) Patent No.: US 10,722,187 B2
(45) Date of Patent: Jul. 28, 2020

(54) SYSTEM AND METHOD FOR IMAGING A SUBJECT

(71) Applicant: GENERAL ELECTRIC COMPANY, Schenectady, NY (US)

(72) Inventors: Remy Klausz, Neuilly sur Seine (FR); Xavier Mancardi, Paris (FR); Yann Le Meur, Versailles (FR); Fanny Patoureaux, Beynes (FR)

(73) Assignee: General Electric Company, Schenectady, NY (US)

( * ) Notice: Subject to any disclaimer, the term of this patent is extended or adjusted under 35 U.S.C. 154(b) by 70 days.

(21) Appl. No.: 16/119,159

(22) Filed: Aug. 31, 2018

(65) Prior Publication Data

US 2020/0069261 A1 Mar. 5, 2020

(51) Int. Cl.
| | | |
|---|---|---|
| *A61B 6/00* | (2006.01) | |
| *A61B 6/02* | (2006.01) | |
| *A61B 6/03* | (2006.01) | |
| *G06T 11/00* | (2006.01) | |
| *G06T 15/08* | (2011.01) | |

(52) U.S. Cl.
CPC .............. *A61B 6/027* (2013.01); *A61B 6/025* (2013.01); *A61B 6/032* (2013.01); *A61B 6/469* (2013.01); *A61B 6/488* (2013.01); *A61B 6/54* (2013.01); *G06T 11/003* (2013.01); *G06T 15/08* (2013.01)

(58) Field of Classification Search
CPC .......... A61B 6/027; A61B 6/025; A61B 6/54; A61B 6/032; A61B 6/469; A61B 6/488; G06T 11/003; G06T 15/08
See application file for complete search history.

(56) References Cited

U.S. PATENT DOCUMENTS

| | | | | |
|---|---|---|---|---|
| 5,457,724 A | * | 10/1995 | Toth | A61B 6/032 378/205 |
| 8,971,493 B2 | * | 3/2015 | Zhang | A61B 5/7285 378/150 |
| 2003/0095624 A1 | | 5/2003 | Eberhard | |
| 2013/0235970 A1 | * | 9/2013 | Voland | G01N 23/046 378/4 |
| 2016/0038113 A1 | * | 2/2016 | Fan | A61B 6/037 378/19 |
| 2016/0106382 A1 | | 4/2016 | Lu | |
| 2016/0199010 A1 | | 7/2016 | Hoernig | |

(Continued)

OTHER PUBLICATIONS

A Review of Breast Tomosynthesis Part I: The Image Acquisition Process published Jan. 4, 2013 by Ioannis Sechopoulos.

(Continued)

*Primary Examiner* — Kiho Kim

(57) ABSTRACT

A system for imaging is provided. The system includes an x-ray source, a detector, and a controller. The x-ray source is operative to transmit x-rays through a subject while the x-ray source continuously travels along a path defined by a sweep angle. The detector is operative to receive the x-rays after having passed through the subject. The controller is operative to: acquire preliminary data regarding the subject via the x-ray source and the detector; determine at least one acquisition parameter from the preliminary data; and acquire one or more projections of the subject via the x-ray source and the x-ray detector based at least in part on the acquisition parameter.

20 Claims, 8 Drawing Sheets

(56) References Cited

U.S. PATENT DOCUMENTS

2017/0065238 A1* 3/2017 Smith .................... A61B 6/025
2018/0049714 A1   2/2018 Nett
2018/0353151 A1* 12/2018 Tang ..................... A61B 6/545

OTHER PUBLICATIONS

A Review of Breast Tomosynthesis Part II: Image Reconstruction, Processing and Analysis, and Advanced Applications published Jan. 4, 2013 by Ioannis Sechopoulos.

Measurements of System Sharpness for Two Digital Breast Tomosynthesis Systems published Nov. 2, 2012 by N.W. Marshall & H. Bosmans.

European Search Report dated Jan. 31, 2020 for European application No. 19194214.3, filed Aug. 28, 2019; 7 pages.

* cited by examiner

SYSTEM AND METHOD FOR IMAGING A SUBJECT

BACKGROUND

Technical Field

Embodiments of the invention relate generally to medical technologies, and more specifically, to a system and method for imaging a subject.

Discussion of Art

Digital tomosynthesis is an imaging technology that provides for volume data acquisition from selected regions of a body. Many tomosynthesis imaging systems include a mobile arm that moves an x-ray source along a curved and/or linear path with respect to a subject such that a plurality of projection images of a body part are obtained. A digital processor then reconstructs a three-dimensional ("3D") image of the subject from the projection images. Unlike traditional computed tomography ("CT"), which involves the reconstruction of a 3D image from projection images that form a complete circumference around the subject, the projection images utilized in tomosynthesis imaging systems typically form a partial circumference, i.e., an arc, as opposed to a full circle.

Many traditional tomosynthesis imaging systems acquire projection images via a "step and shoot" image acquisition technique, i.e., the x-ray source is moved to and stopped at one or more positions along a path, whereupon a projection image is acquired at each position with the x-ray source stationary during emission of an x-ray beam. As will be appreciated, the projections acquired via step and shoot scans are typically immune from motion blurring artifacts, also referred to herein simply as "motion blur." Other traditional tomosynthesis systems acquire projections via "continuous sweep" scanning, i.e., projections are acquired at one or more positions along the path without stopping the x-ray source. While continuous sweep scans on average have shorter scan times than step and shoot scans, the projections acquired via continuous sweep scans generally have a high risk of experiencing motion blur.

In order to reduce the risk of incurring motion blur, many traditional tomosynthesis systems perform continuous sweep scans using the same tightly controlled predetermined parameters for each scan. While use of the same predetermined parameters for each scan reduces the risk of motion blur in many continuous scans, it may result in motion blurring for situations where the "scan speed", i.e., the speed of the x-ray source along the path, and the "pulse duration", i.e., the time period of a single electromagnetic radiation exposure, results in the x-ray source moving sufficiently far enough, e.g., about one (1) mm, along the path during a single exposure/pulse. Accordingly, the scan speed and/or pulse duration of many traditional continuous scan tomosynthesis systems are limited. In other words, the use of the same predetermined parameters for each scan by traditional tomosynthesis systems limits the "acquisition speed" of the scanning procedure, i.e., how fast a tomosynthesis system can scan a subject.

What is needed, therefore, is an improved system and method for imaging a subject.

BRIEF DESCRIPTION

In an embodiment, a system for imaging is provided. The system includes an x-ray source, a detector, and a controller. The x-ray source is operative to transmit x-rays through a subject while the x-ray source continuously travels along a path defined by a sweep angle. The detector is operative to receive the x-rays after having passed through the subject. The controller is operative to: acquire preliminary data regarding the subject via the x-ray source and the detector; determine at least one acquisition parameter from the preliminary data; and acquire one or more projections of the subject via the x-ray source and the x-ray detector based at least in part on the acquisition parameter.

In another embodiment, a method for imaging is provided. The method includes acquiring preliminary data of a subject via a controller, an x-ray source, and an x-ray detector. The x-ray source is operative to transmit x-rays through the subject while the x-ray source continuously travels along a path defined by a sweep angle. The detector is operative to receive the x-rays after having passed through the subject. The method further includes determining at least one acquisition parameter from the preliminary data via the controller; and acquiring one or more projections of the subject via the controller, the x-ray source, and the detector based at least in part on the acquisition parameter.

In yet another embodiment, a non-transitory computer readable medium storing instructions is provided. The stored instructions adapt a controller to acquire preliminary data from a subject via an x-ray source and a detector. The x-ray source is operative to transmit x-rays through the subject while the x-ray source continuously travels along a path defined by a sweep angle. The detector is operative to receive the x-rays after having passed through the subject. The stored instructions further adapt the controller to: determine at least one acquisition parameter from the preliminary data; and acquire one or more projections of the subject via the x-ray source and the x-ray detector based at least in part on the acquisition parameter.

DRAWINGS

The present invention will be better understood from reading the following description of non-limiting embodiments, with reference to the attached drawings, wherein below:

DETAILED DESCRIPTION

Figure 1:
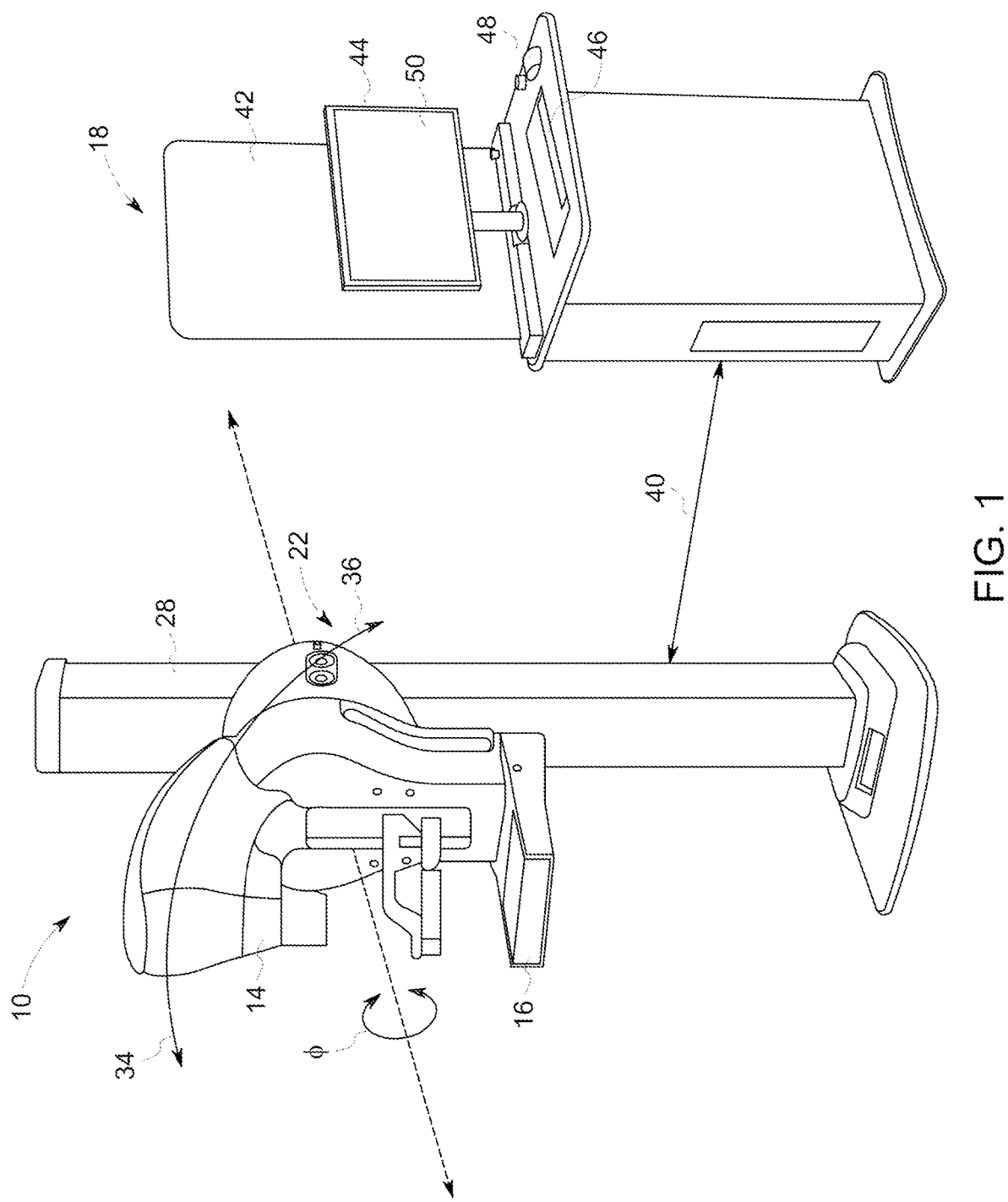
FIG. 1 is a schematic diagram of a system for imaging a subject, in accordance with an embodiment of the present invention.

Reference will be made below in detail to exemplary embodiments of the present invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "scan," "procedure," and/or "imaging procedure" refer to the acquisition of data by an imaging system from which one or more images of a subject may be generated from. The term "acquisition parameter," as used herein, means a setting of a device or a property of a subject to be imaged that affects the operation of an imaging system. As also used herein, the terms "continuous sweep" and/or "continuous sweep scanning", refer to a method of acquiring images via an imaging system in which the x-ray source moves along a path with respect to the corresponding x-ray detector in a continuous manner, i.e., projections are acquired at one or more positions along the path without stopping the x-ray source. The term "preliminary data", as used herein, refers to data concerning the characteristics of a subject that affect imaging of the subject, e.g., attenuation, size, shape, density, etc.

Additionally, while the embodiments disclosed herein are described with respect to an x-ray based imaging system, e.g., a tomosynthesis imaging system, it is to be understood that embodiments of the present invention are equally applicable to other devices and/or imaging systems which preform tomography, have low tolerances for parameter settings, and/or have difficult to calculate parameters. Further, embodiments of the present invention related imaging systems may be used to analyze objects within any material which can be internally imaged, generally. As such, embodiments of the present invention are not limited to analyzing objects within human tissue.

Referring now to FIG. 1, the major components of a system 10 for imaging a subject/patient 12 (FIG. 2), in accordance with an embodiment of the present invention, are shown. In this embodiment, system 10 is a mammogram machine configured for tomosynthesis although, as will be appreciated, other configurations/embodiments (FIGS. 2-6) are disclosed herein. As shown in FIG. 1, the system 10 includes an x-ray source 14, an x-ray detector 16, and a controller 18. The x-ray source 14 is operative to transmit x-rays 20 (FIG. 2) through the subject 12 (FIG. 2) while the x-ray source 14 continuously travels along a path 22 defined by a sweep angle Ø with a start position 34 and an end/stop position 36 (both of which may be interchangeable). The x-ray detector 16 is operative to receive the x-rays 20 after having passed through the subject 12. As will be appreciated, and explained in greater detail below, the controller 18 is operative to acquire preliminary data regarding/from the subject 12 via the x-ray source 14 and detector 16, determine at least one acquisition parameter from the preliminary data, and acquire one or more projections/images of the subject 12 based at least in part on the acquisition parameter. In other words, embodiments of the present invention acquire projections of the subject 12 via a continuous sweep with acquisition parameters that have been tailored/customized to the subject 12 based on preliminary data acquired from the subject 12.

The controller 18 may be a workstation having at least one processor and a memory device as shown in FIG. 1 or, in other embodiments, the controller 18 may be embedded/integrated into one or more of the various components of the system 10 disclosed above. In embodiments, the controller 18 may be in electrical communication with the x-ray source 14, x-ray detector 16, and/or a sensor 24 (FIG. 2) via an electrical and/or optical communication connection 40. The connection 40 may be a wired and/or wireless connection. As will be appreciated, in embodiments, the controller 18 may include a radiation shield 42 that protects an operator of the system 10 from the x-rays 20 emitted by the x-ray source 14. The controller 18 may further include a display 44, a keyboard 46, mouse 48 and/or other appropriate user input devices, that facilitate control of the system 10 via a user interface 50, e.g., a graphical user interface ("GUI"). Data regarding the x-rays 20 received by the x-ray detector 16 may be electrically communicated to the controller 18 from the x-ray detector 16 via cable/electronic connection 40 such that the controller 18 generates/reconstructs one or more images which may be shown on the display 44.

Figure 2:
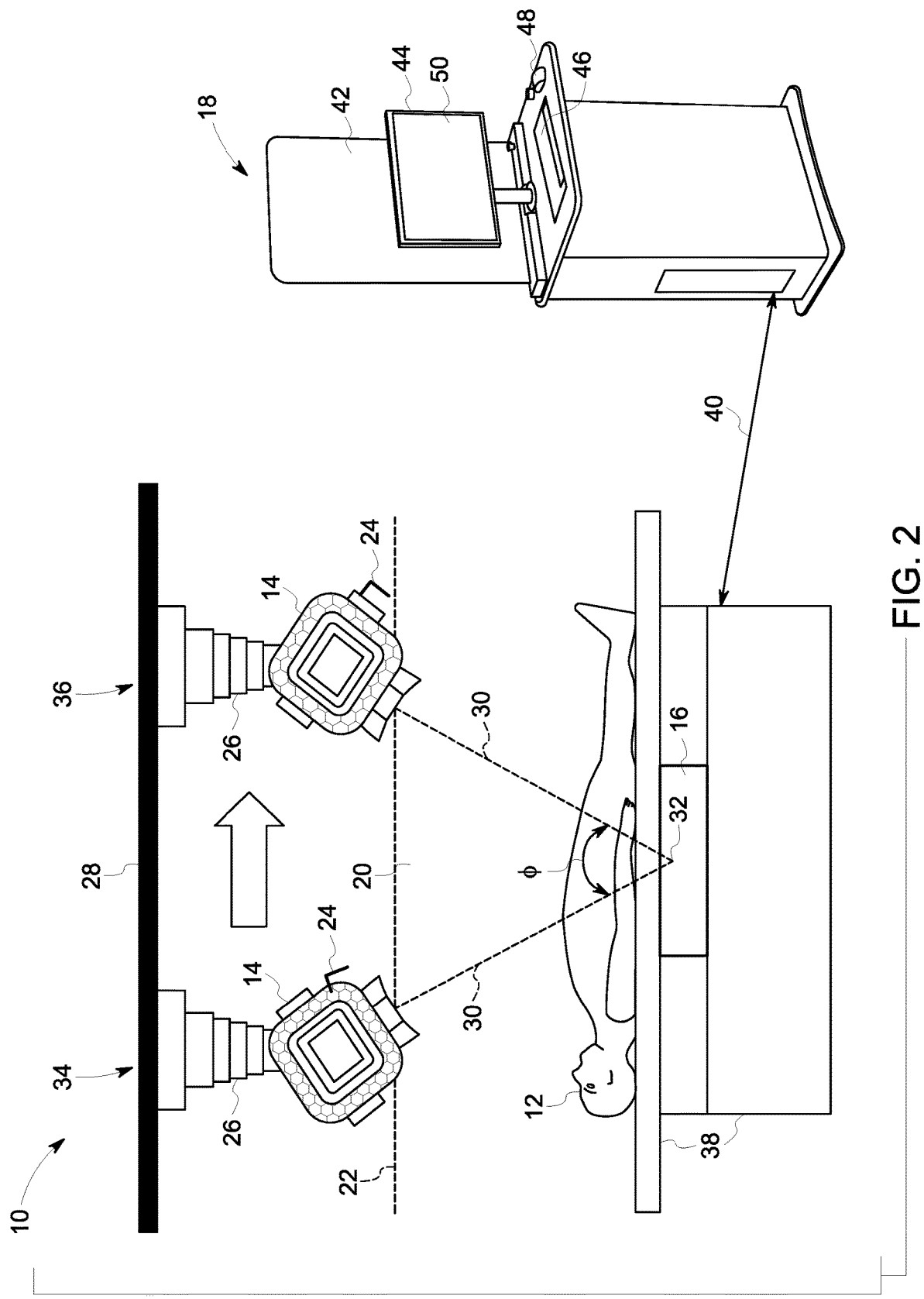
FIG. 2 is a schematic diagram of another embodiment of the system of FIG. 1, in accordance with an embodiment of the present invention.
Figure 3:
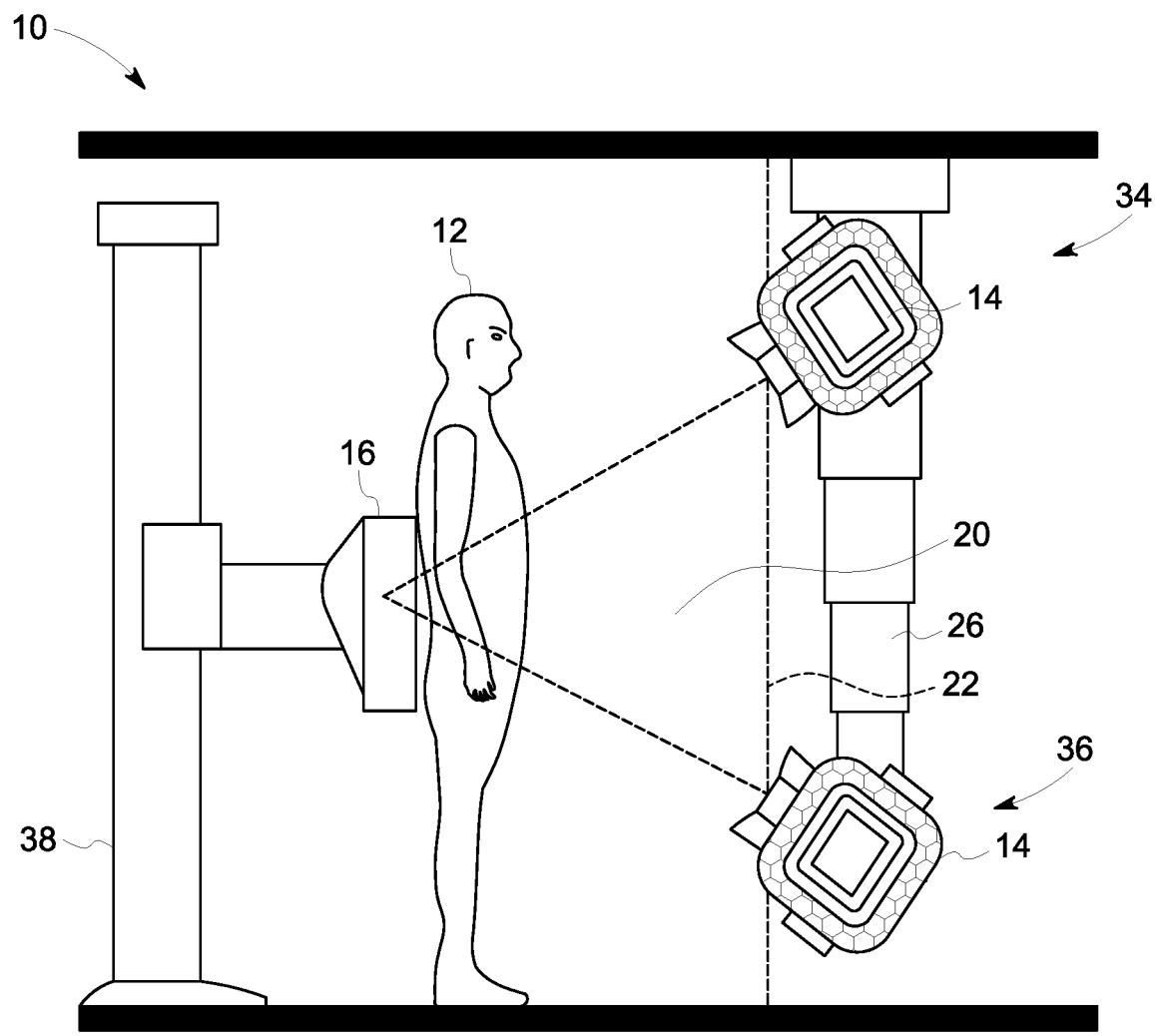
FIG. 3 is a schematic diagram of yet another orientation of the system of FIG. 2, in accordance with an embodiment of the present invention.
Figure 4:
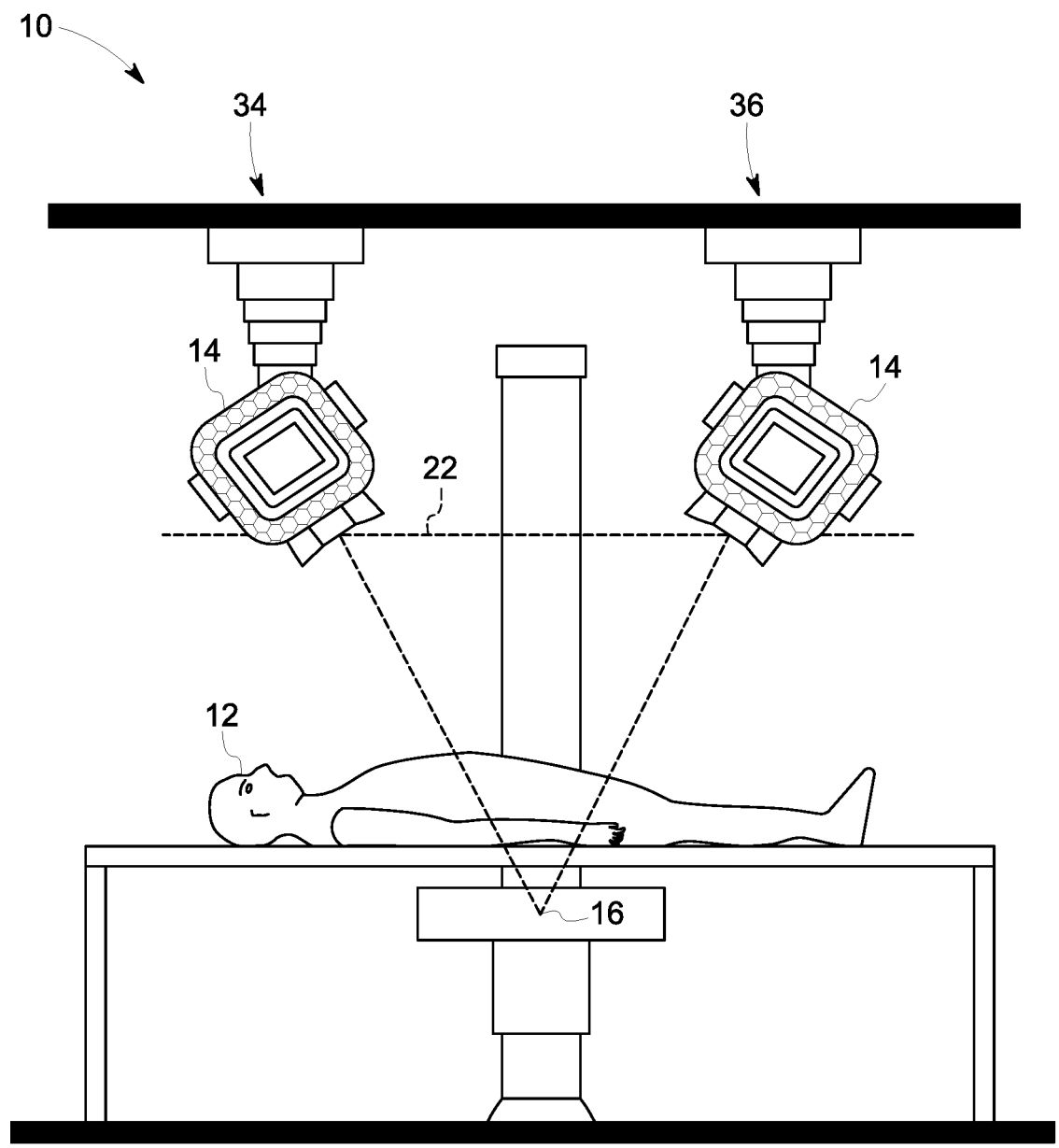
FIG. 4 is a schematic diagram of still yet another orientation of the system of FIG. 2, in accordance with an embodiment of the present invention.
Figure 5:
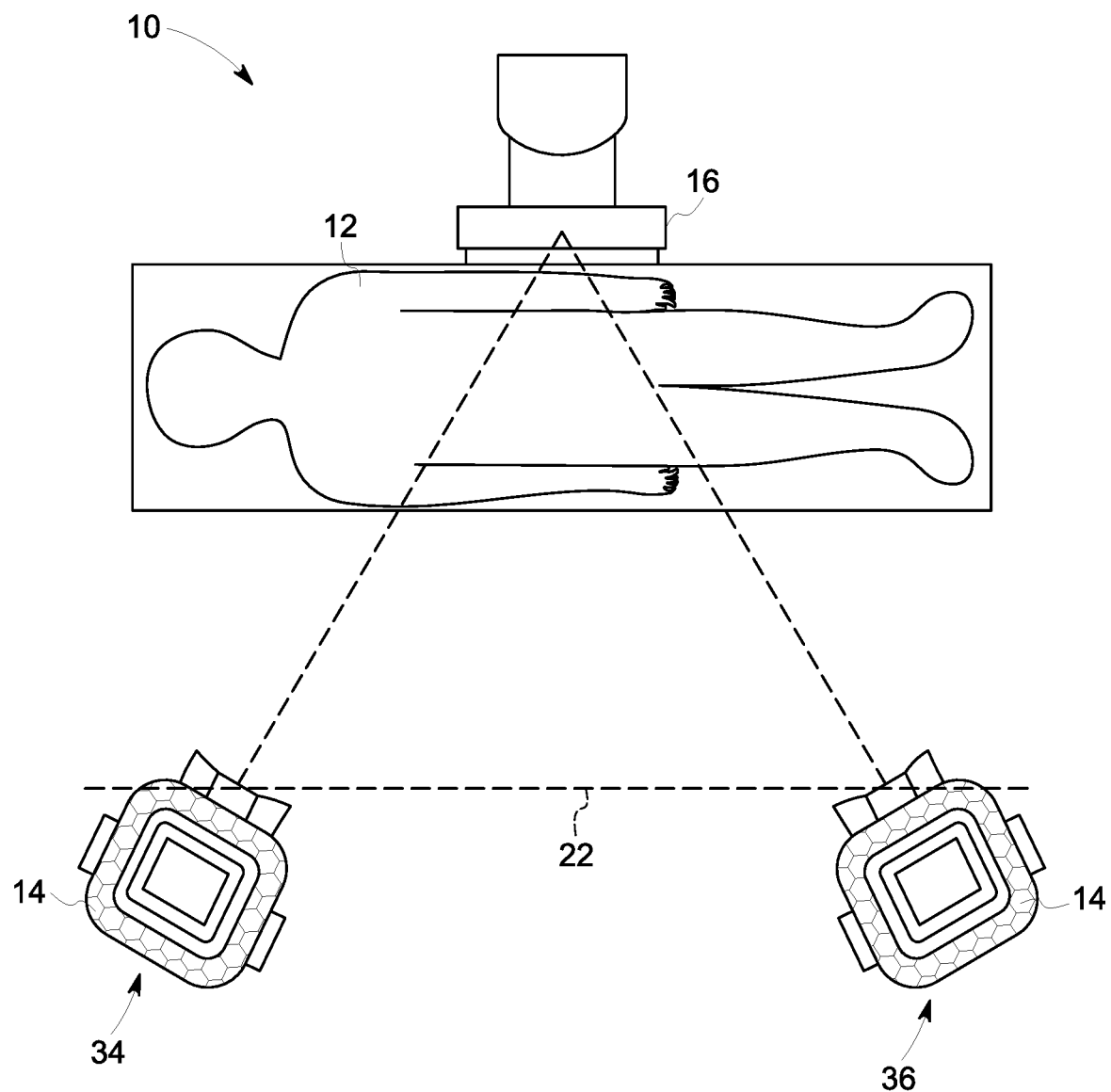
FIG. 5 is a schematic diagram of still yet another orientation of the system of FIG. 2, in accordance with an embodiment of the present invention.

Accordingly, as shown in FIG. 2, in embodiments, the system 10 may further include a sensor 24, which may be disposed on the x-ray source 14, that is operative to acquire the preliminary data. The x-ray source 14 may be rotatably mounted to a mobile arm 26 secured to a support structure 28, e.g., a mount and/or the ceiling of a room, such that the x-ray source 14 is able to train the x-rays 20 along a line of projection 30, i.e., the center line of the rays 20, that continuously intersects a target location 32 on the x-ray detector 16 as the mobile arm 26 moves the x-ray source 14 along the path 22. The path 22 may have a start position 34 and an end/stop position 36 such that the line of projection 30 sweeps an area of the subject 12 defined by the sweep angle Ø. As will be appreciated, while the path 22 is shown herein as being linear, it will be understood that, in other embodiments, the path 22 may have a curved shape, e.g., the system 10 may be mammogram machine as shown in FIG. 1, and/or any other shape configured for tomosynthesis. Further, the sweep angle Ø may be less than 365°, and in some embodiments, may be between about 0° to 180°, 20° to 100°, 20° to 80°, 20° to 40°, or 20° to 30°. As will be appreciated, in some embodiments, the sweep angle Φ may be greater than or equal to 365°.

Figure 6:
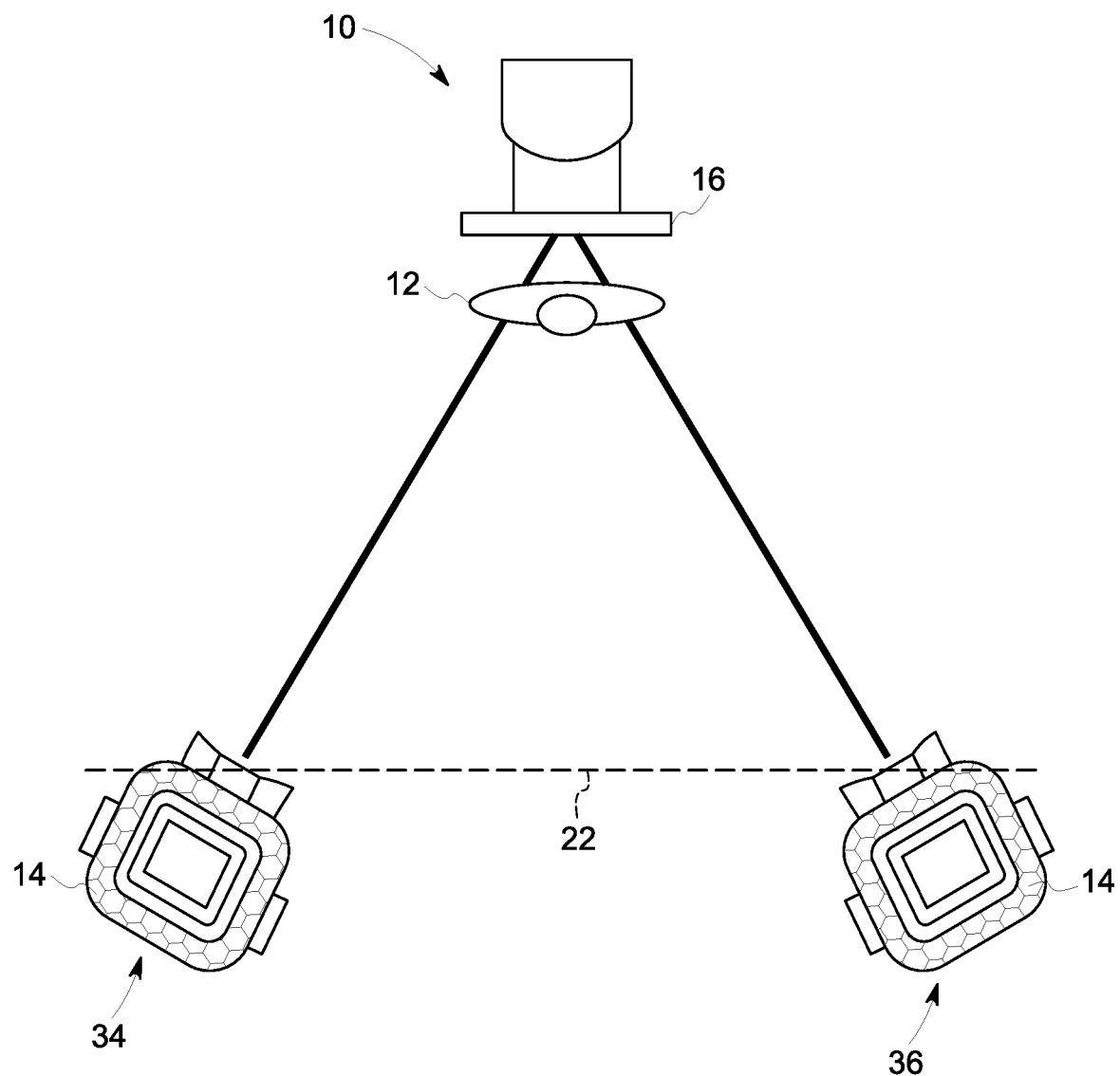
FIG. 6 is a schematic diagram of still yet another orientation of the system of FIG. 2, in accordance with an embodiment of the present invention.

As further shown in FIG. 2, the x-ray detector 16 is positioned opposite the x-ray source 14 such that the subject 12 is disposed between the x-ray source 14 and the x-ray detector 16. While the x-ray detector 16 is depicted herein as being stationary with respect to the subject 12, it will be understood, that, in other embodiments, the x-ray detector 16 moves in relation to the subject 12 (e.g., the rotation about axis 1 as illustrated in FIG. 1 of x-ray source 14 and x-ray detector 16). Additionally, the x-ray detector 16 may be integrated into a subject support structure 38, e.g., a table and/or other platform structure which, in embodiments, may be operative to support the entire subject 12 or a part of the subject 12. For example, as shown in FIGS. 1-6, in embodiments, the system 10 may be configured to perform: a mammography sweep (FIG. 1), a table horizontal sweep (FIG. 2) for supine imaging, a wallstand vertical sweep (FIG. 3) for upright imaging, a table side sweep (FIG. 4) for supine imaging, a wallstand cross-table sweep for cross-table imaging of a patient laying down (FIG. 5) and/or standing (FIG. 6).

Figure 7:
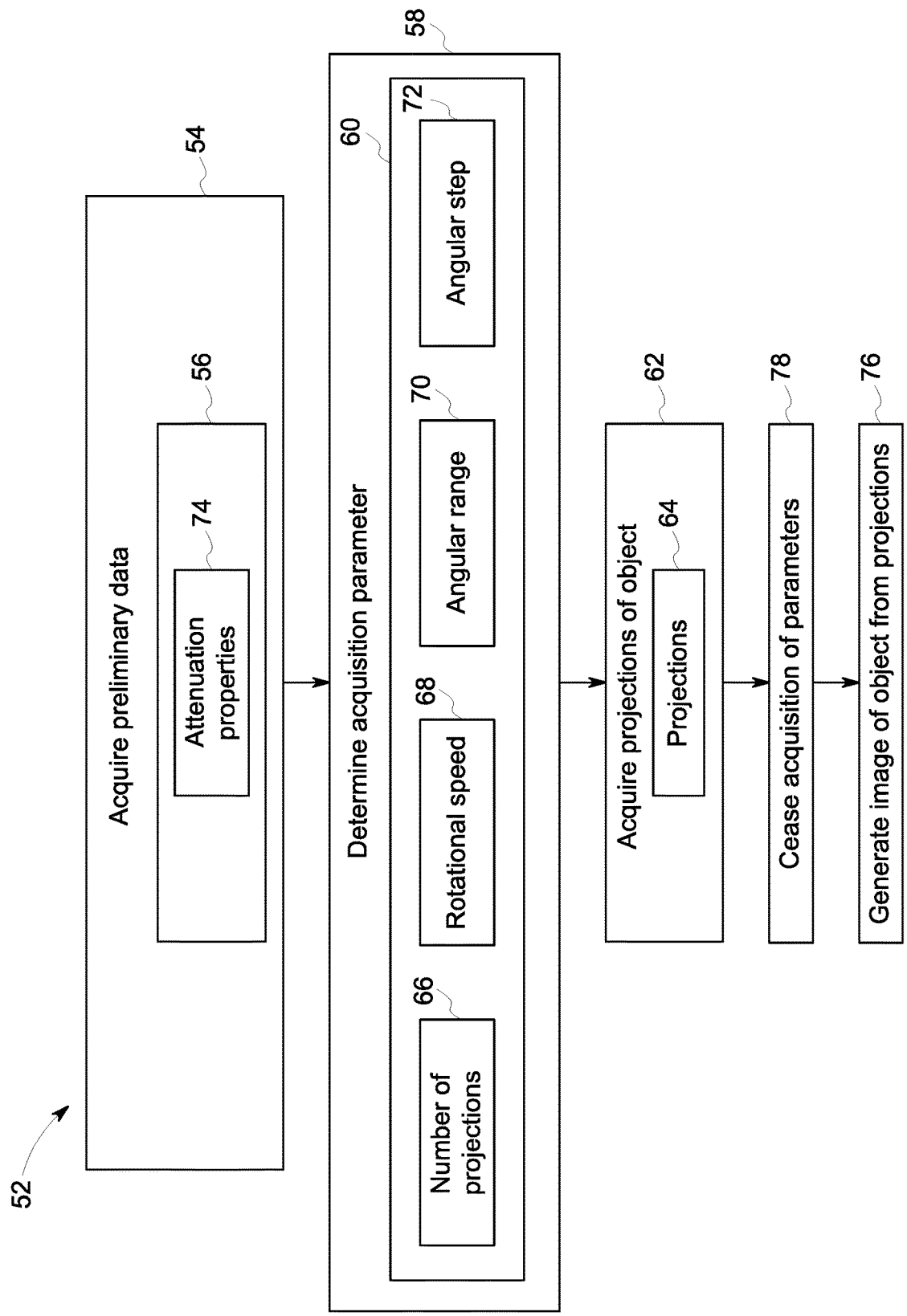
FIG. 7 is a flow chart depicting a method for imaging a subject utilizing the system of FIG. 1, in accordance with an embodiment of the present invention.

Referring now to FIGS. 1, 2, and 7; a method 52 (FIG. 7) for imaging the subject 12 (FIG. 2) utilizing the system 10 (FIG. 1) is shown. The method 52 includes acquiring 54 the preliminary data 56 regarding/of/from the subject 12 via the controller 18, x-ray source 14, and the detector 16, while the x-ray source 14 continuously travels along the path 22. The method 52 further includes determining 58 the at least one acquisition parameter 60 from/based at least in part on the preliminary data 56. The method 52 further includes acquiring 62 one or more projections 64 of the subject 12 via the controller 18, x-ray source 14, and detector 16 based at least in part on the acquisition parameter 60.

Accordingly, as shown in FIG. 7, in embodiments, the acquisition parameter 60 may be: a number of projections 66, i.e., the number of projections acquired by the x-ray source 14 and the detector 16 as the x-ray source 14 travels along the path 22 in a continuous manner; a rotational speed 68 of the x-ray source 14, i.e., the speed at which the x-ray source 14 rotates along the path 22 such that the rays 20 (FIG. 2) stay trained on the target location 32 (FIG. 2); an angular range 70 of the x-ray source 14, i.e., the angular distance between the centerline 30 (FIG. 2) of the rays 20 to the target 32 (FIG. 2) at the first position 34 (FIG. 2) and the centerline 30 (FIG. 2) of the rays 20 to the target 32 at the second position 36 (FIG. 2); and/or an angular step 72 between projections of the one or more projections 64, i.e., the distance along the path 22 between individual projections 64 acquired 62 via the x-ray source 14 and the detector 16.

In embodiments, the preliminary data 56 includes an attenuation property 74 of the subject 12, e.g., polymethyl methacrylate-equivalent thickness at densest location ("PMMA"). As will be understood, in embodiments, the attenuation property 74 may be derived from the preliminary data 56 via one or more models, e.g., a look up table containing values for anode material, filter selection, kVp, mAs per pulse and/or time, a rotation speed, and a number of projections. As will be understood, in embodiments, the preliminary data 56 may further include thickness information/data acquired via the sensor 24 and/or derived from the position of a device/component of the system 10, e.g., a compression paddle, with respect to the subject 12.

In embodiments, the method 52 may further include generating 76 a 3D image, e.g., a 3D digital breast tomosynthesis image, from the one or more projections 64 via the controller 18.

As stated above, in some embodiments the sensor 24, may be operative to acquire 54 the preliminary data 56 from the subject 12. Accordingly, in embodiments the sensor 24 may be an optical camera, which acquires an image/picture of the subject 12, i.e., the preliminary data 56 is an optical image. As such, the sensor 24 may be mounted on the x-ray source 14, e.g., an x-ray tube, on the mobile arm 26, support structure 28, and/or in any other manner so as to provide clear access, e.g., a line of sight, from the sensor 24 to the subject 12. As will be appreciated, in such embodiments, the sensor 24 may be operative to image the subject 12 with visible, infrared, ultra-violet, and/or other forms of electromagnetic radiation suitable for imaging the subject 12. Further, the sensor 24 may acquire a single image and/or a plurality of images. In embodiments, the sensor 24 may acquire a geometry, e.g., a plurality of points along a surface of the subject 12 wherein the points may or may not constitute an image.

In embodiments, the preliminary data may be acquired 54 during a pre-shot/pre-exposure, which, as used herein, means an image of the subject 12 acquired by the x-ray source 14 and the detector 16 and analyzed prior to the system 10 acquiring 62 subsequent projection/images of the subject 12. For example, in an embodiment, the pre-shot may be a low resolution two-dimensional ("2D") image acquired via a lower x-ray dose than images which are subsequently acquired via the x-ray source 14 and detector 16 and used to make a medical diagnosis. Additionally, the pre-shot may include multiple views of the subject 12.

In certain aspects, the preliminary data 54 may come from outside the system 10. For example, in embodiments, the preliminary data may be a radiology medical image, e.g., an x-ray, digital tomosynthesis, magnetic resonance image ("MRI"), positron emission tomographic ("PET") image, and/or any other type of medical image, acquired by a different imaging system, or by the same imaging system at a different time, and saved in a database accessible to the controller 18. Similarly, the controller 18 may access additional data concerning the subject 12, e.g., patient medical histories stored in a database external to the room in which the system 10 is housed. Further, in certain aspects, an artificial intelligence ("AI") and/or deep learning algorithm may be utilized to process and/or obtain the preliminary data. For example, in embodiments, such an algorithm may generate/obtain the preliminary data by analyzing medical information, to include pre-acquired images, pulled from a database, as described above.

In embodiments, determining 58 the acquisition parameter 60 may be based on one of an anode material of the x-ray source 14, a peak kilovoltage ("kVp") of the x-ray source 14, a milliamps ("mA") per pulse of the x-ray source 14, i.e., the integral of a current flowing through a ray tube/generator of the source 14 during a pulse which may be in milliampere-seconds ("mAs"); and/or a number of projections, e.g., a desired number of projections to be acquired by the x-ray source 14 and the detector 18. As will be understood, in some embodiments, the acquisition parameter 60 may be determined 58 based on input received by the controller 18 via the keyboard 46, mouse 48, or other suitable input device, e.g., a touch screen. For example, the system 10 may acquire and show an optical image of the subject 12 on the display 44, and an operator of the system 10 may then select a portion of the subject 12 in the image, which in turn, may be used by the controller 18 to adjust one or more of the acquisition parameters disclosed herein.

In embodiments, the method 52 further includes ceasing 78 acquisition of the one or more projections when the number of projections acquired by the x-ray source 14 and the detector 16 is equal to a desired number of projections, or when a rotational angle of the x-ray source, i.e., the angle between the center line 30 of the rays 20 and the detector 16 reaches a desired degree/rotational angle.

Thus, in operation according to an embodiment, the subject 12 is placed onto and/or in front of the detector 16. The controller 18 then acquires 54 the preliminary data 56 from the subject 12 via a pre-scan. The controller 18 then determines 58 one or more acquisition parameters 60, e.g., the number of desired projections 66, the rotational speed 68, the angular range 70, and/or the angular step 72, from one or more attenuation properties 74 derived from the preliminary data 56. The controller 18 then begins to acquire 62 the projections 64 by accelerating the x-ray source 14 along the path 22 until a desired speed/rotational speed is reached. When at the desired speed/rotational speed, the controller 18 then begins to acquire the projections 64 in accordance with the determined 58 acquisition parameters 60. Upon acquiring the desired number of projections, and/or reaching a desired rotational angle, the controller 18 ceases 78 acquisition of the projections. Having obtained the projections, the controller 18 then proceeds to generate 76 a 3D image of the subject 12 from the projections.

Thus, as will be appreciated, some embodiments of the present invention fractionate, i.e., split/divide, the total x-ray exposure to the subject 12 over a relatively large number of individual exposures, e.g., typically twenty (20) to thirty (30) and/or, in embodiments, up to fifty (50), which in turn, provides for the ability to deviate from the need to acquire the exact/calculated number of desired projections and/or to deviate from the desired/calculated rotational angle.

It is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the system may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

Figure 8:
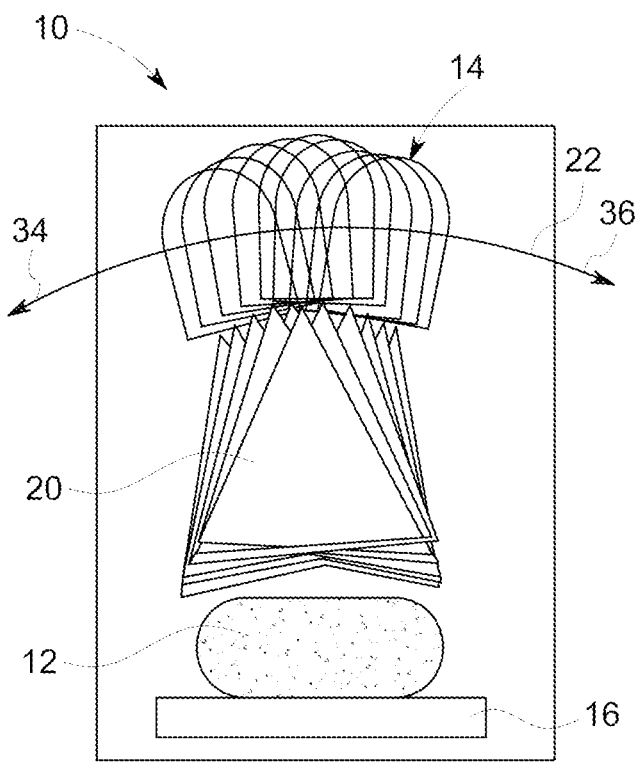
FIG. 8 is a schematic diagram of a generic system for imaging a subject demonstrating step-and-shoot image acquisition.
Figure 9:
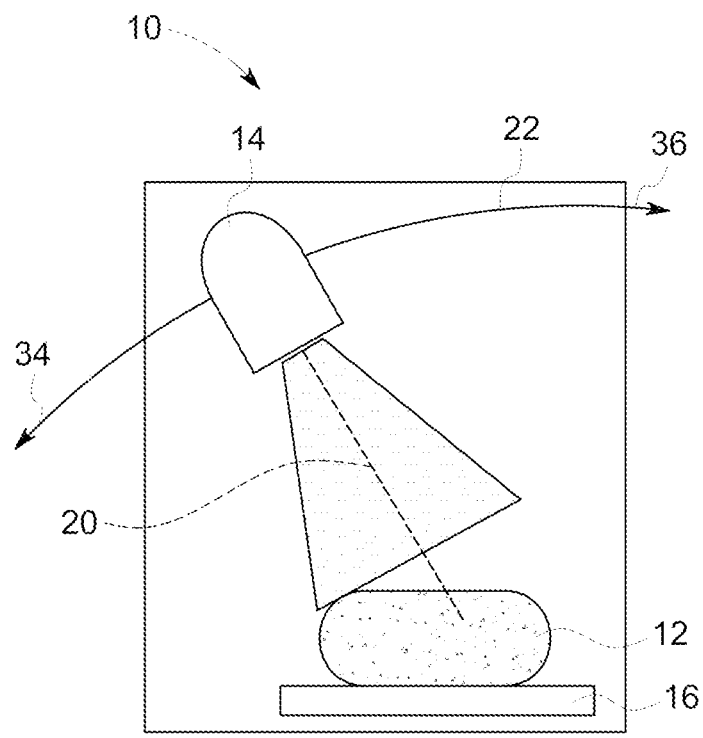
FIG. 9 is a schematic diagram of a generic system for imaging a subject demonstrating continuous sweep scanning.

Finally, FIGS. 8 and 9 respectively illustrate examples of step-and-shoot (FIG. 8) and continuous sweep scanning (FIG. 9) of an x-ray source 14 disposed over a subject 12 supported by an x-ray detector 16. The x-ray source 14 moves along path 22 having start position 34 and end position 36 and emits x-rays 20. As seen in the step-and-shoot example depicted in FIG. 8, the x-ray detector 14 makes a series of individual stops along the path 22 in order to acquire projections of the subject 12, which is in contrast to the motion illustrated in FIG. 9 wherein the x-ray source 14 acquires projections of the subject 12 while continuously moving along path 22.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for imaging a subject is provided. The system includes an x-ray source, a detector, and a controller. The x-ray source is operative to transmit x-rays through the subject while the x-ray source continuously travels along a path defined by a sweep angle. The detector is operative to receive the x-rays after having passed through the subject. The controller is operative to: acquire preliminary data regarding the subject via the x-ray source and the detector; determine at least one acquisition parameter from the preliminary data; and acquire one or more projections of the subject via the x-ray source and the x-ray detector based at least in part on the acquisition parameter. In certain embodiments, the acquisition parameter is at least one of a number of projections, a rotational speed of the x-ray source, an angular range of the x-ray source, and an angular step between projections of the one or more projections. In certain embodiments, the preliminary data includes an attenuation property of the subject. In certain embodiments, the attenuation property is polymethyl methacrylate-equivalent thickness at densest location. In certain embodiments, the controller determines the at least one acquisition parameter based at least in part on one of an anode material of the x-ray source, a filter selection of the x-ray source, a peak kilovoltage of the x-ray source, a milliamps per pulse of the x-ray source, a rotational speed of the x-ray source, and a number of projections. In certain embodiments, the controller is further operative to generate a three-dimensional image from the one or more projections. In certain embodiments, the path is configured for tomosynthesis. In certain embodiments, the controller is further operative to cease acquisition of the one or more projections when a number of the one or more projections acquired by the x-ray source and the detector is equal to a desired number of projections, or when a rotational angle of the x-ray source reaches a desired rotational angle.

Other embodiments provide for a method for imaging a subject. The method includes acquiring preliminary data of the subject via a controller, an x-ray source, and an x-ray detector. The x-ray source is operative to transmit x-rays through the subject while the x-ray source continuously travels along a path defined by a sweep angle. The detector is operative to receive the x-rays after having passed through the subject. The method further includes determining at least one acquisition parameter from the preliminary data via the controller; and acquiring one or more projections of the subject via the controller, the x-ray source, and the detector based at least in part on the acquisition parameter. In certain embodiments, the acquisition parameter is at least one of a number of projections, a rotational speed of the x-ray source, an angular range of the x-ray source, and an angular step between projections of the one or more projections. In certain embodiments, the preliminary data includes an attenuation property of the subject. In certain embodiments, the attenuation property is polymethyl methacrylate-equivalent thickness at densest location. In certain embodiments, determining at least one acquisition parameter from the preliminary data via the controller is based at least in part on one of an anode material of the x-ray source, a filter selection of the x-ray source, a peak kilovoltage of the x-ray source, a milliamps per pulse of the x-ray source, a rotational speed of the x-ray source, and a number of projections. In certain embodiments, the method further includes generating a three-dimensional image from the one or more projections via the controller. In certain embodiments, the method further includes ceasing acquisition of the one or more projections when a number of the one or more projections acquired by the x-ray source and the detector is equal to a desired number of projections, or when a rotational angle of the x-ray source reaches a desired rotational angle.

Yet still other embodiments provide for a non-transitory computer readable medium storing instructions. The stored instructions adapt a controller to acquire preliminary data from a subject via an x-ray source and a detector. The x-ray source is operative to transmit x-rays through the subject while the x-ray source continuously travels along a path defined by a sweep angle. The detector is operative to receive the x-rays after having passed through the subject. The stored instructions further adapt the controller to: determine at least one acquisition parameter from the preliminary data; and acquire one or more projections of the subject via the x-ray source and the x-ray detector based at least in part on the acquisition parameter. In certain embodiments, the acquisition parameter is at least one of a number of projections, a rotational speed of the x-ray source, an angular range of the x-ray source, and an angular step between projections of the one or more projections. In certain embodiments, the preliminary data includes an attenuation property of the subject. In certain embodiments, the attenuation property is polymethyl methacrylate-equivalent thickness at densest location. In certain embodiments, determination of the at least one acquisition parameter is based at least in part on one of an anode material of the x-ray source, a filter selection of the x-ray source, a peak kilovoltage of the x-ray source, a milliamps per pulse of the x-ray source, a rotational speed of the x-ray source, and a number of projections.

Accordingly, as will be appreciated, by leveraging information acquired during a preliminary scan/pre-scan of the subject, some embodiments of the present invention provide for optimized acquisition parameters for continuous sweep scans in order to reduce the risk of motion blur artifacts, which in turn, provides for faster scan times, longer pulse/exposures times, and/or shorter acquisition times for continuous scan tomosynthesis. In other words, some embodiments of the present invention provide for improved scan times with less motion blur by tailoring the acquisition sequence of a continuous tomosynthesis imaging system to the subject being scanned, as opposed to traditional systems which often implement a one-size-fits all approach.

As will be further appreciated, by customizing/tailoring the acquisition sequence to the subject being scanned, e.g., increasing/decreasing the number of projections to be acquired and/or adjusting the rotational speed, some embodiments of the present invention reduce the individual exposure times of each projection, which in turn provides for lower x-ray doses to the subject for a given image quality, as compared to traditional imaging systems. Thus, some embodiments of the present invention seek to adjust the balance tradeoff between speed/dose and image quality Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their subjects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for imaging comprising:
an x-ray source operative to transmit x-rays through a subject while the x-ray source continuously travels along a path defined by a sweep angle;
a detector operative to receive the x-rays after having passed through the subject; and a controller operative to:
acquire preliminary data regarding the subject via the x-ray source and the detector;
determine at least one acquisition parameter from the preliminary data; and
acquire one or more projections of the subject via the x-ray source and the x-ray detector based at least in part on the acquisition parameter;
wherein the controller determines the at least one acquisition parameter based on an anode material of the x-ray source.

2. The system of claim 1, wherein the acquisition parameter is at least one of a number of projections, a rotational speed of the x-ray source, an angular range of the x-ray source, and an angular step between projections of the one or more projections.

3. The system of claim 1, wherein the preliminary data includes an attenuation property of the subject.

4. The system of claim 3, wherein the attenuation property is polymethyl methacrylate-equivalent thickness at densest location.

5. The system of claim 1, wherein the controller determines the at least one acquisition parameter further based at least in part on one of a filter selection of the x-ray source, a peak kilovoltage of the x-ray source, a milliamps per pulse of the x-ray source, a rotational speed of the x-ray source, and a number of projections.

6. The system of claim 1, wherein the controller is further operative to:
generate a three-dimensional image from the one or more projections.

7. The system of claim 1, wherein the path is configured for tomosynthesis.

8. The system of claim 1, wherein the controller is further operative to:
cease acquisition of the one or more projections when a number of the one or more projections acquired by the x-ray source and the detector is equal to a desired number of projections, or when a rotational angle of the x-ray source reaches a desired rotational angle.

9. A method for imaging comprising:
acquiring preliminary data of a subject via a controller, an x-ray source, and an x-ray detector, the x-ray source operative to transmit x-rays through the subject while the x-ray source continuously travels along a path defined by a sweep angle, the detector operative to receive the x-rays after having passed through the subject;
determining at least one acquisition parameter from the preliminary data via the controller; and
acquiring one or more projections of the subject via the controller, the x-ray source, and the detector based at least in part on the acquisition parameter,
wherein determining at least one acquisition parameter from the preliminary data via the controller is based on an anode material of the x-ray source.

10. The method of claim 9, wherein the acquisition parameter is at least one of a number of projections, a rotational speed of the x-ray source, an angular range of the x-ray source, and an angular step between projections of the one or more projections.

11. The method of claim 9, wherein the preliminary data includes an attenuation property of the subject.

12. The method of claim 11, wherein the attenuation property is polymethyl methacrylate-equivalent thickness at densest location.

13. The method of claim 9, wherein determining at least one acquisition parameter from the preliminary data via the controller is further based at least in part on one of a filter selection of the x-ray source, a peak kilovoltage of the x-ray source, a milliamps per pulse of the x-ray source, a rotational speed of the x-ray source, and a number of projections.

14. The method of claim 9 further compromising:
generating a three-dimensional image from the one or more projections via the controller.

15. The method of claim 9 further comprising:
ceasing acquisition of the one or more projections when a number of the one or more projections acquired by the x-ray source and the detector is equal to a desired number of projections, or when a rotational angle of the x-ray source reaches a desired rotational angle.

16. A non-transitory computer readable medium storing instructions that adapt a controller to:
acquire preliminary data from a subject via an x-ray source and a detector, the x-ray source operative to transmit x-rays through the subject while the x-ray source continuously travels along a path defined by a sweep angle, the detector operative to receive the x-rays after having passed through the subject;
determine at least one acquisition parameter from the preliminary data; and
acquire one or more projections of the subject via the x-ray source and the x-ray detector based at least in part on the acquisition parameter,
wherein determination of the at least one acquisition parameter is based on an anode material of the x-ray source.

17. The non-transitory computer readable medium of claim 16, wherein the acquisition parameter is at least one of a number of projections, a rotational speed of the x-ray source, an angular range of the x-ray source, and an angular step between projections of the one or more projections.

18. The non-transitory computer readable medium of claim 16, wherein the preliminary data includes an attenuation property of the subject.

19. The non-transitory computer readable medium of claim 18, wherein the attenuation property is polymethyl methacrylate-equivalent thickness at densest location.

20. The non-transitory computer readable medium of claim 16, wherein determination of the at least one acquisition parameter is further based at least in part on one of a filter selection of the x-ray source, a peak kilovoltage of the x-ray source, a milliamps per pulse of the x-ray source, a rotational speed of the x-ray source, and a number of projections.

* * * * *